United States Patent [19]

Taylor

[11] 4,243,680

[45] Jan. 6, 1981

[54] METHOD OF REDUCING INFESTATION OF CITRUS RUST MITES ON CITRUS TREES

[75] Inventor: James L. Taylor, DeLand, Fla.

[73] Assignee: Thompson-Hayward Chemical Company, Kansas City, Kans.

[21] Appl. No.: 10,274

[22] Filed: Feb. 7, 1979

[51] Int. Cl.$^3$ .............................................. A01N 47/28
[52] U.S. Cl. ..................................................... 424/322
[58] Field of Search ........................................ 424/322

[56] References Cited

U.S. PATENT DOCUMENTS

| | | | |
|---|---|---|---|
| 3,748,356 | 7/1973 | Wellinga et al. | 424/322 |
| 4,085,226 | 4/1978 | Sirrenberg et al. | 424/322 |
| 4,139,636 | 2/1979 | Sirrenberg et al. | 424/322 |

*Primary Examiner*—Douglas W. Robinson
*Attorney, Agent, or Firm*—Norman N. Spain

[57] ABSTRACT

A method of reducing the population of the citrus rust mite on citrus trees by treating the trees with such substituted benzoyl phenyl ureas as N-(2,6-difluorobenzoyl)-N'-(3-fluoro-4-chloro-phenyl) urea and N-(2,6-difluorobenzoyl)-N'-(4-chloro-phenyl) urea.

15 Claims, No Drawings

METHOD OF REDUCING INFESTATION OF CITRUS RUST MITES ON CITRUS TREES

BACKGROUND OF THE INVENTION

This invention relate to a method for reducing the infestation of citrus rust mite (*Phyllocoptruta oleivora*) on the leaves and on the fruit of citrus trees.

In U.S. Pat. No. 3,748,356 there are disclosed various benzoyl phenyl urea derivatives. These compounds are disclosed in this patent to be useful in controlling insect populations. It is further stated in this patent that these compounds are useful in that they interfere with the mechanism of metamorphoses of insects and thus prevent development of the insects.

Among these insects are *Aedes aegypti, Leptinotarsa decemlineata, Pieris brassica, Musca domestica* and *Schistocerca gregaria*.

Nothing is said in this patent about any effect of these compounds on mites and there is nothing said in this patent on the effect of these compounds of the development of the citrus rust mite.

Attempts have been made to control the infestation of citrus rust mites with such miticides as Chlorobenzilate, Carzol, Acarol, Ethion and sulphur. However, these attempts have not been too successful since these materials while attacking the adult stages of the mite do not attack the developmental stages and thus, in the absence of frequent spraying, do not prevent population growth throughout the crop season.

SUMMARY OF THE INVENTION

It is an object of this invention to provide an improved method for reducing the infestation of citrus trees by the citrus rust mite and in particular one that requires a minimum of spraying.

According to the invention it has unexpectedly been found that selected compounds of the above-mentioned U.S. Pat. No. 3,748,356 are highly useful in preventing the development of the citrus rust mite and are of value in reducing the infestation of citrus fruit trees by this mite.

More particularly there has been found that the following benzoyl phenyl urea compounds of this patent are highly useful in preventing the development of citrus rust mites:

N-(2,6-difluorobenzoyl)-N'-(3-fluoro-4-chlorophenyl) urea;
N-(2,6-difluorobenzoyl)-N'-(4-chlorophenyl) urea;
N-(2,6-dichlorobenzoyl)-N'-(4-trifluoromethylphenyl) urea;
N-(2,6-difluorobenzoyl)-N'-(3,4-dichlorophenyl) urea;
N-(2,6-dichlorobenzoyl)-N'-(3-fluoro-4-bromo-phenyl) urea;
N-(2,6-dichlorobenzoyl)-N'-(3-fluoro-4-iodophenyl) urea;
N-(2,6-dichlorobenzoyl)-N'-(ethyl)-N'-(4-bromophenyl) urea;
N-(2,6-dichlorobenzoyl)-N'-(2-fluoro-4-iodophenyl) urea;
N-(2,6-dichlorobenzoyl)-N'-(methyl)-N'-(4-chorophenyl) urea;
N-(2,6-dichlorobenzoyl)-N'-(ethyl)-N'-(4-chlorophenyl) urea;
N-(2,6-difluorobenzoyl)-N'-(4-bromophenyl) urea;
N-(2,6-difluorobenzoyl)-N'-(4-trifluoromethylphenyl) urea;
N-(2,6-difluorobenzoyl)-N'-(3-trifluoromethylphenyl) urea; and
N-(2,6-difluorobenzoyl)-N'-(methyl)-N'-(4-fluorophenyl) urea.

DESCRIPTION OF THE PREFERRED EMBODIMENTS

It has been found that the benzoyl phenyl urea derivatives of the invention are useful, in even very low concentrations, of significantly reducing the infestation of citrus rust mite on the leaves and fruit of citrus trees without the manifestation of any undesirable activity.

These derivatives, in particular N-(2,6-difluorobenzoyl)-N'-(4-chlorophenyl) urea, have been found to reduce citrus rust mite populations by causing a high degree of second instar nymphal mortality while producing little or no adult mortality.

These benzoyl phenyl urea derivatives may be employed in concentrations of 1 to 20 oz per acre, however, it has been found that concentrations of 5 to 10 oz per acre are particularly useful for best results.

These benzoyl phenyl urea derivatives may be applied to citrus trees in forms well known in the art. Thus these compounds may be dispersed in a solid or liquid carrier material, or diluted in a liquid carrier material and, if desired, combined with adjuvants such as surface-active substances, crop oil and stabilizers.

Examples of forms in which these compounds may be applied to the citrus trees are aqueous suspensions or dispersions, oil suspensions or oil dispersions, dusts and invert emulsions.

The oil suspensions and oil dispersions, aqueous suspensions and oil dispersions are made from highly concentrated primary compositions such as wettable powder, miscible oils and solutions.

The invert emulsions are mainly used in air application, large surface areas being treated with a comparatively small amount of composition. A short time before, or even during the spraying, the invert emulsion may be prepared in the spraying apparatus by emulsifying water in an oil solution or in an oil dispersion of the active substance.

Dusts are obtainable by intimately mixing the active substance with an inert solid carrier material in a concentration of, for example, from 1–50% by weight. Examples of suitable solid carrier materials are talc, kaolin, pipeclay, diatom earth, dolomite, gypsum, chalk, bentonite, attapulgite and colloidal $SiO_2$ or mixtures of these and similar substances. Alternatively organic carrier materials may be used such as, for example, ground walnut shells.

Wettable powders are produced by mixing from 10–80 parts by weight of a solid inert carrier such as, for example, one of the aforementioned carrier materials with from 10–80 parts by weight of the active substance, from 1–5 parts by weight of a dispersing agent such, for example, as the lignin sulfonates or alkyl naphthalene sulfonates known for this purpose, and preferably also with from 0.5–5 parts by weight of a wetting agent such as one of the fatty alcohol sulfates, alkylaryl sulfonates or fatty acid condensation products, for examples those sold under the trademark Igepon.

The wettable powders are dispersed or suspended in water and diluted to the desired concentration for application for citrus trees.

To produce miscible oils the active substance is dissolved or finely dispersed in a suitable solvent which may be poorly miscible with water after which an emulsifier is added to the solution. Examples of suitable solvents are xylene, toluene, high-aromatic petroleum distillates, for example solvent naphtha, distilled tar oil and mixtures of these liquids. Examples of emulsifiers are alkylphenoxypolyglycol ethers, polyoxyethylene sorbitan esters of fatty acids or polyoxyethylene sorbitol esters of fatty acids. In these miscible oils the concentration of the active compound is not restricted within narrow limits and may vary between, say, 2% and 50% by weight.

Oil suspensions are made by forming a dispersion of the miscible oil in a suitable liquid such as a paraffinic oil and adding a stabilizer to the dispersion.

In addition to being a miscible oil the liquid and highly concentrated primary composition may be a solution of the active substance in a satisfactorily water-miscible liquid, for example acetone, to which solution a dispersing agent and possibly a wetting agent is added. Dilution with water shortly before or during the spraying operation results in an aqueous dispersion of the active substance.

Besides the above-mentioned ingredients the compositions according to the invention may contain other substances known for use in compositions of this type.

For example, a lubricant such as calcium stearate or magnesium stearate may be added to a wettable powder. Also, "adhesives" such as polyvinyl alcohol cellulose derivatives or other colloidal materials, such as casein, may be added to improve the adherence of the pesticide to the surface to be protected.

If a more rapid elimination of the citrus rust mite population is desired, the benzoyl phenyl urea derivatives of the instant invention may be combined with such well known miticides as Chlorobenzilate, Carzol, Acarol, Ethion, and sulphur.

A representative compound of this invention, N-(2,6-difluorobenzoyl)-N'-(4-chlorophenyl) urea (TH-6040) was tested on a citrus crop, specifically a pink grapefruit crop. In this test the citrus trees were sprayed until runoff with the following: TH-6040 in a concentration of 2 oz. per 100 gallons of water, 4 oz. of TH-6040 per 100 gallons of water, TH-6040 in concentrations of 2 oz. and 4 oz. per 100 gallons of water containing in addition 0.5% of citrus spray oil and in combination with Galecron (chlordimeform) at a concentration of 1 oz. of the Galecron and 1 oz. of the TH-6040 in 100 gallons of water. Further for comparison the trees were sprayed with Chlorobenzilate in the concentration of 2 oz. in 100 gallons of water.

The percentage of infestation and population density were determined by a hand lens examination of fruits and leaves. Both percentage infestation and population densities were determined by examining 25 fruit per replicates with 4 replicate utilized. The population density ratings (PD) are 0=0, 1=low, 2=moderate and 3=high. The rating 0 is given to a count of no mites, 1 to a count of less than 10 mites per cm$^2$, 2 to a count on 10–100 mites per cm$^2$ and 3 to a count of greater than 100 mites per cm$^2$.

Pretreatment counts indicated are a high population density with high infestation levels. The treatments were evaluated over a period of 105 days with data collected every 21 days, the tests being terminated after 105 days due to a decline in the natural citrus rust mite populations and irregular distributions of the population throughout the treatment area.

Data regarding effects on percent infestation and population density are summarized below:

| Treatment | Rate | | PRE | Day After Treatment | | | | | |
|---|---|---|---|---|---|---|---|---|---|
| | | | | 7 | 28 | 42 | 56 | 77 | 105 |
| TH-6040 | 2 oz. | % | 81.6 | 25.3 | 10.8 | 6.6 | 1.6 | 11.6 | 13.3 |
| | | PD | 2.5 | 1.0 | 0.8 | 0.3 | 0.1 | 0.6 | 0.5 |
| TH-6040 | 4 oz. | % | 87.5 | 29.1 | 3.3 | 3.3 | 11.6 | 6.6 | 6.6 |
| | | PD | 2.5 | 1.0 | 0.4 | 0.2 | 0.8 | 0.5 | 0.6 |
| TH-6040 + | 2 oz. | % | 18.3 | 6.6 | 15.0 | 10.0 | 3.3 | 3.3 | |
| | | | 87.5 | | | | | | |
| OIL | 5% | PD | 2.3 | 1.0 | 0.8 | 0.8 | 0.8 | 0.3 | 0.5 |
| TH-6040 + | 4 oz. | % | 89.2 | 30.8 | 5.0 | 7.5 | 3.3 | 5.0 | 5.8 |
| OIL | 5% | PD | 2.2 | 1.0 | 0.6 | 0.5 | 0.3 | 0.3 | 0.5 |
| TH-6040 + | 1 oz. | % | 90.8 | 22.5 | 6.6 | 5.8 | 11.6 | 3.3 | 12.5 |
| GALECRON | 1 oz. | PD | 2.5 | 0.8 | 0.8 | 0.5 | 0.6 | 0.3 | 1.0 |
| CBL | 2 oz. | % | 90.0 | 73.3 | 76.6 | 70.0 | 73.3 | 53.3 | 58.3 |
| | | PD | 2.0 | 1.5 | 1.8 | 1.8 | 1.1 | 1.3 | 1.3 |
| CHECK | — | % | 87.5 | 99.1 | 73.3 | 90.0 | 78.0 | 72.0 | 48.0 |
| | | PD | 2.5 | 2.7 | 1.8 | 1.8 | 1.4 | 1.4 | 1.2 |

% = Percent Infestation
PD = Population Density
PRE = Prior to Spraying
CBL = Chlorobenzilate It will be apparent that various modifications may be made to the method of the present invention without departing from its scope as defined by the following claims.

What we claim is:

1. A method of reducing infestation of citrus crops by citrus rust mites comprising subjecting the developmental stages of said mites located on said citrus crops to the action of a composition comprising a miticidally effective amount of a compound selected from the group consisting of N-(2,6-difluorobenzoyl)-N'-(3-fluoro-4-chlorophenyl) urea;

N-(2,6-dichlorobenzoyl)-N'-(4-chlorophenyl) urea;

N-(2,6-dichlorobenzoyl)-N'-(4-trifluoromethylphenyl) urea;

N-(2,6-difluorobenzoyl)-N'-(3,4-dichlorophenyl) urea;

N-(2,6-dichlorobenzoyl)-N'-(3-fluoro-4-bromo-phenyl) urea;

N-(2,6-dichlorobenzoyl)-N'-(3-fluoro-4-iodophenyl) urea;

N-(2,6-dichlorobenzoyl)-N'-(ethyl)-N'-(4-bromophenyl) urea;

N-(2,6-dichlorobenzoyl)-N'-(2-fluoro-4-iodophenyl) urea;

N-(2,6-dichlorobenzoyl)-N'-(methyl)-N'-(4-chlorophenyl) urea;
N-(2,6-dichlorobenzoyl)-N'-(ethyl)-N'-(4-chlorophenyl) urea;
N-(2,6-difluorobenzoyl)-N'-(4-bromophenyl) urea;
N-(2,6-difluorobenzoyl)-N'-(4-trifluoromethylphenyl) urea;
N-(2,6-difluorobenzoyl)-N'-(3-trifluoromethylphenyl) urea; and
N-(2,6-difluorobenzoyl)-N'-(methyl)-N'-(4-fluorophenyl) urea
and a finely divided inert carrier therefor.

2. The method of claim 1 wherein the compound is N-(2,6-difluorobenzoyl)-N'-(3-fluoro-4-chlorophenyl) urea.

3. The method of claim 1 wherein the compound is N-(2,6-difluorobenzoyl)-N'-(4-chlorophenyl) urea.

4. The method of claim 1 wherein the compound is N-(2,6-dichlorobenzoyl)-N'-(4-trifluoromethylphenyl) urea.

5. The method of claim 1 wherein the compound is N-(2,6-difluorobenzoyl)-N'-(3,4-dichlorophenyl) urea.

6. The method of claim 1 wherein the compound is N-(2,6-dichlorobenzoyl)-N'-(3-fluoro-4-bromo-phenyl) urea.

7. The method of claim 1 wherein the compound is N-(2,6-dichlorobenzoyl)-N'-(3-fluoro-4-iodophenyl) urea.

8. The method of claim 1 wherein the compound is N-(2,6-dichlorobenzoyl)-N'-(ethyl)-N'-(4-bromophenyl) urea.

9. The method of claim 1 wherein the compound is N-(2,6-dichlorobenzoyl)-N'-(2-fluoro-4-iodophenyl) urea.

10. The method of claim 1 wherein the compound is N-(2,6-dichlorobenzoyl)-N'-(methyl)-N'-(4-chorophenyl) urea.

11. The method of claim 1 wherein the compound is N-(2,6-dichlorobenzoyl)-N'-(ethyl)-N'-(4-chlorophenyl) urea.

12. The method of claim 1 wherein the compound is N-(2,6difluorobenzoyl)-N'-(4bromophenyl) urea.

13. The method of claim 1 wherein the compound is N-(2,6-difluorobenzoyl)-N'-(4-trifluoromethylphenyl) urea.

14. The method of claim 1 wherein the compound is N-(2,6-difluorobenzoyl)-N'-(3-trifluoromethylphenyl) urea.

15. The method of claim 1 wherein the compound is N-(2,6-difluorobenzoyl)-N'-(methyl)-N'-(4-fluorophenyl) urea.

* * * * *